US005124149A

United States Patent [19]

Shapiro et al.

[11] Patent Number: 5,124,149

[45] Date of Patent: Jun. 23, 1992

[54] COMPOSITIONS AND METHODS FOR BIOCONTROL USING FLUORESCENT BRIGHTENERS

[75] Inventors: Martin Shapiro, Columbia, Md.; Edward Dougherty, Alexandria, Va.; John J. Hamm, Tifton, Ga.

[73] Assignee: The United States of America as represented by the Secretary of Agriculture, Washington, D.C.

[21] Appl. No.: 609,848

[22] Filed: Nov. 7, 1990

[51] Int. Cl.[5] ...................... C09B 26/00; A01N 25/00; A01N 63/00; A61K 37/48

[52] U.S. Cl. ................................ 424/93 T; 424/94.1; 424/405; 8/648

[58] Field of Search ...................... 424/93, 94.1, 195.1, 424/405; 8/648

[56] References Cited

U.S. PATENT DOCUMENTS

| | | | |
|---|---|---|---|
| 2,089,413 | 7/1935 | Paine . | |
| 2,171,427 | 5/1937 | Leipzig . | |
| 3,911,110 | 10/1975 | Smirnoff | 424/93 |
| 4,205,525 | 11/1987 | Abel | 8/555 |
| 4,295,850 | 10/1981 | Häberli | 8/524 |
| 4,304,569 | 12/1981 | Engelhardt | 8/584 |

OTHER PUBLICATIONS

Villaume, F. G., J. Am. Oil Chem. Soc., vol. 35, (1958), pp. 558-566.

J. Econ Entomology 78:982-987, 1985, Laboratory Evaluation of New Ultraviolet absorbers for protection of Douglas-Fir Tussock Moth Baculovirus, Martignoni, Mauro E.

Shapiro, M., J. Econ. Entomol., vol. 82, No. 2, (1989) pp. 548-550.

Selitrennikoff, C. P., Experimental Mycology, vol. 8, (1984) pp. 269-272.

Haigler et al., Science, vol. 218, (1980), pp. 903-905.

Roncero et al., J. Bacteriol., vol. 163, No. 3, (1985), pp. 1180-1185.

Green et al., Laboratory Medicine, vol. 18, No. 7, (1987), pp. 456-458.

*Primary Examiner*—Ronald W. Griffin
*Assistant Examiner*—Ralph G. Gitomer
*Attorney, Agent, or Firm*—M. Howard Silverstein; John D. Fado; Janelle S. Graeter

[57] ABSTRACT

The present invention relates to compositions and methods of their use for the management or biocontrol on insect pests. The compositions comprise an entomopathogen and a chitin synthetase inhibitor alone or in combination with a UV protectant. Alternatively, compositions are disclosed comprising an entomopathogen and a fluorescent brightener of the stilbene type which may have chitin synthetase inhibitory properties. Specifically, entomopathogens such as Nuclear polyhedrosis viruses (NPV), Cytoplasmic polyhedrosis viruses (CPV), Entomopox viruses (EPV) and Granulosis viruses (GV) and iridescent virus (IV) are protected from UV radiation and their biological activity enhanced using fluorescent brighteners analogs, particularly, 4, 4'-diamino-2, 2'-stilbene disulfonic acid.

16 Claims, No Drawings

COMPOSITIONS AND METHODS FOR BIOCONTROL USING FLUORESCENT BRIGHTENERS

BACKGROUND OF THE INVENTION

1. Field of the Invention

This invention relates to the use of entomopathogens such as viruses, bacteria, protozoa, fungi and nematodes formulated with adjuvants in compositions, as biocontrol agents.

2. Description of the Prior Art

Biocontrol agents are attractive alternatives to chemical pesticides for subduing plant pests. Their specificity for the host pest minimizes their environmental impact from a pollution standpoint. However, entomopathogens used in formulations as biocontrol agents suffer from instability after exposure to solar radiation, especially in the ultraviolet (UV) portion of the spectrum. The resulting loss of biological activity prolongs the rate at which insect pests are killed. In many instances, the pathogens lose 50% of their original activity within days.

Another important barrier to the use of biocontrol agents, especially viruses, in the management of insect pests, is that entomopathogenic viruses inherently act slowly even without the loss of activity due to UV radiation, usually requiring several days or more to achieve mortality. Larvae feed and continue to defoliate or destroy crops until shortly before death. As an example, the gypsy moth, *Lymantria dispar* is an insect pest of extreme environmental concern in North America, causing widespread defoliation. A nuclear polyhedrosis virus (NPV), the gypsy moth's natural entomopathogen, has been used as a biocontrol agent registered in the United States as Gypchek [Lewis, et al., U.S. For. Serv. Pap., NE-441, (1979), 9 pp.; Lewis et al., U.S. For. Serv. Pap., NE-447, (1979), 8 pp.]. Although NPV is successful in reducing gypsy moth populations, the virus is very slow acting, allowing larvae to feed almost two weeks after exposure. Therefore, field applications of virus do not provide adequate crop or foliage protection. Greater foliage protection may occur if viral activity could be increased by the addition of adjuvants [Doane and Wallis, J. Insect. Pathol., Vol. 6, (1964), pp. 423-429; Yadava, Z. Angew., Entomol., Vol. 65, (1970), pp. 175-183; Shapiro, et al., Ann., Entomol. Soc. Am., Vol. 75, (1982), pp. 346-349]. Thus, there is a need to provide biocontrol agents which provide improved environmental stability and accelerated rates of insect kill.

Several attempts have been made to increase the stability of biocontrol agents by adding UV screens such as uric acid [Teetor and Kramer, J. Invertebr. Pathol., Vol. 30, (1977), pp. 348-353; B vitamins, Shapiro, M., Environ. Entomol., Vol. 14, (1985), pp. 705-708; Congo red, Shapiro, M., J. Econ. Entomol. Vol. 82, No. 2, (1989), pp. 548-550) and activity enhancers and boric acid, Shapiro, et al., Ann. Entol. Soc. Amer., Vol. 75, No. 3, (1982), pp. 346-349] and Chitinase [Shapiro, et al., J. Econ. Entomol., Vol. 80, No. 6, (1987), pp. 1113-1116]. While these formulations provided some protection, there was still loss of activity resulting from inactivation by UV radiation. Nuclearpolyhedrosis virus (NPV) was protected using the commercially available stilbene fluorescent brightener, Tinopal DCS, at a concentration of 5% [Martignoni and Iwai, J. Econ. Entomol., Vol. 78, (1985), pp. 982-987]. While the brightener provided protection at high concentration, it did not affect pest mortality.

Stilbene fluorescent brighteners inhibit cellulose [Roberts, et al., J. Cell Biology, Vol. 9, (1981), p. 115a] and chitin [Herth, C., J. Cell Biol., Vol. 87, (1980), pp. 442-450] microfibril formation. However, these brighteners are not known as adjuvants for biocontrol. Calcofluor White prevents the assembly of cellulose microfibrils in *Acetobacter xylinum* by hydrogen bonding with glucan chains [Haigler, et al., Science, Vol. 210, No. 4472, (1980), pp. 903-906] and inhibits chitin synthetase activity in *Neurospora crassa* [Selitrennikoff, C. P., Exp. Mycol., Vol. 8, (1984), pp. 269-272].

While Calcofluor White interacts with a number of polysaccharides [Wood, P. J., Carbohydr. Res., Vol. 81, (1980), pp. 271-287] it has a high affinity for chitin and cellulose.

It can be seen from the prior art, there is an urgent need for the formulation of entomopathogens into compositions that enhance their activity.

SUMMARY OF THE INVENTION

We have discovered that inhibitors of chitin synthetase, and particularly certain fluorescent brighteners, especially compounds of the stilbene type, specifically, derivatives of 4,4'-diamino-2,2'-stilbene disulfonic acid and their salts provide protection for entomopathogens from the damaging effects of exposure to UV radiation as well as decreasing the mortality time and lethal dose in the host insect. It is therefore an object of the present invention to provide biocontrol compositions using fluorescent brighteners that (a) increase the pathogen persistence to UV radiation, and (b) increase its virulence in the host, thus overcoming the disadvantages described in the prior art. Additionally, there are provided methods for the use of these compositions for the biocontrol or management of insect pests. Surprisingly, it was found that formulating entomopathogens with the addition of these fluorescent brighteners into compositions, enhanced the biological activity or virulence of the viruses that are infective for gypsy moth, alfalfa looper, fall armyworm and celery looper, up to a 1000-fold.

DETAILED DESCRIPTION OF THE INVENTION

In the treatment of insect populations with entomopathogens such as the nuclearpolyhedrosis virus (NPV) from *Heliothis zea*, the cytoplasmic polyhedrosis virus (CPV) from *Heliothis virescens, entomopox virus (EV)* from *Amsacta Moorei* and *granulosis virus* (GV), from *Spodoptera frugiperda*, the iridescent virus from *H. zea* the bacterium *Bacillus thuringiensis*, the fungus *Nomuraea rileyi* and the protozoan *Vairimorpha nectarix*, an adjuvant is required to negate the effect of UV radiation.

The methodology used in testing potential adjuvants was described by Shapiro, et al., Environ. Entomol., Vol. 12, No. 3, (1983), pp. 982-985 and incorporated herein by reference.

The potential adjuvants tested were those known to have fluorescent brightening activity. Optical, or fluorescent brighteners absorb invisible UV radiation and re-emit visible blue light. The parent stilbene molecules (illustrated below) spatial arrangement of electrons and specific ring groups contribute to the molecule's absorbance in UV and fluorescence in the visible portion of the spectrum.

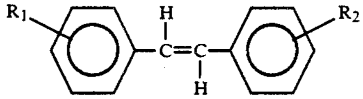

$R_1$ and $R_2$ groups such as amino, alkoxy, hydroxyl, halogen and sulfonic acid additionally contribute to fluorescence.

[Villaume, F. G., J. Am. Oil Chemists Soc., Vol. 35, (1958), pp. 558-566]. Derivatives of stilbene as well as other commercially available fluorescent brighteners were tested in the context of the present invention.

Optical brighteners have been generally catagorized into six major chemical classes:

1) Triazinylstilbenes
2) Aroylstilbenes
3) Benzidinesulfones
4) Bisbenzimidazoles
5) Triazoles
6) Amino coumarins, and illustrated below.

TRIAZINYLSTILBENES

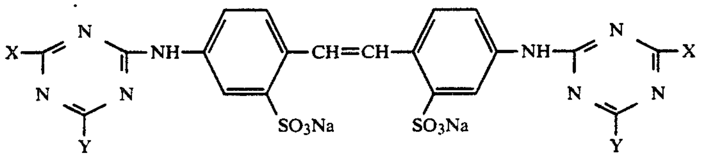

X = Y =

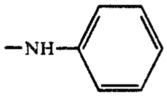

X =

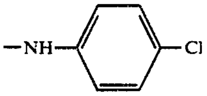

X =

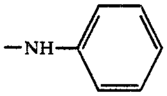

Y = $-N(CH_2CH_2OH)_2$

Y = $-N(CH_2CH_2OH)_2$

Aroylstilbenes

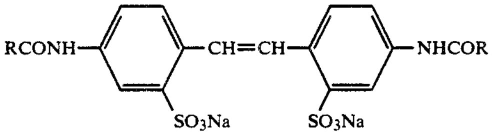

R =

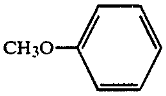

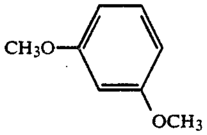

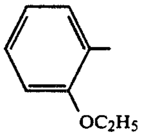

Benzidinesulfones

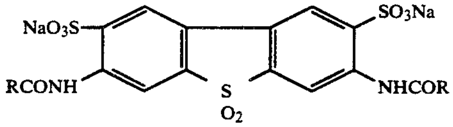

R =

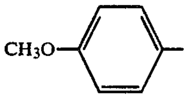

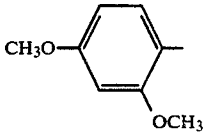

-continued

Bisbenzimidazoles

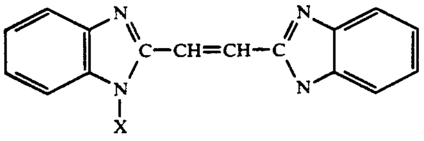

X = H or ALKYL

Triazole

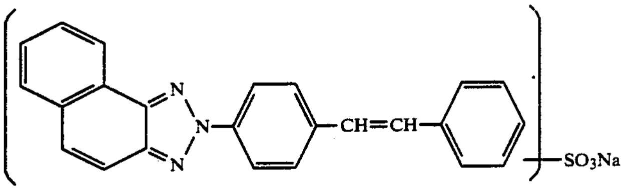

Amino coumarins

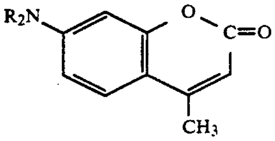

R = ALKYL

EXAMPLE 1

In each of the tests, the percentage of virus-caused mortality was the sole criterion for evaluation of UV protection. Mortality caused by non-irradiated gypsy moth NPV (LdMNPV) in water ($H_2O$) was compared with mortalities caused by irradiated NPV (in $H_2O$ or brighteners at 1% w/v) at different times or at day 14 only. Additionally, UV protection was measured in terms of original activity remaining (OAR), after irradiation. The percentage of original activity (% OAR) was based on mortality before (where LC=100% OAR) and after irradiation.

Twenty-three brighteners were evaluated as UV protectants of LdMNPV (Table 1) by the method of Shapiro, et al., supra. Essentially, a colonized strain of *Lymantria dispar* (*L. dispar*) was used throughout the example. A wheat germ diet was used as the rearing medium [Bell, et al., 1981 the Gypsy Moth: Research Toward Integrated Pest Management, U. S. Dep. Agric. Tech. Bull. (1584), pp. 598-633]. NPV, Hamden isolate LDP-67 from the U.S. Forest Service was used as the biocontrol agent.

TABLE 1

Evaluation of various fluorescent brighteners as radiation protectants.[a, b]

| 10% OAR | 11-30% OAR | 31-50% OAR | 51-70% OAR | 71-90% OAR | 90% OAR |
|---|---|---|---|---|---|
| ABL | COL | EHB | LD | PAL | $M_2R$* |
| NL | RWP | | | ERN | CF* |
| | | | | PAT | BS* |
| | | | | EFR | BSB* |
| | | | | WGS | BSU* |
| | | | | ALA | CL* |
| | | | | PAB | BKL* |

TABLE 1-continued

Evaluation of various fluorescent brighteners as radiation protectants.[a, b]

| 10% OAR | 11-30% OAR | 31-50% OAR | 51-70% OAR | 71-90% OAR | 90% OAR |
|---|---|---|---|---|---|
| | | | | KNR | AR* |

[a]Six replicates: 50 larvae per treatment per replicate NPV used at final concentration of 500,000 PIB/ml. Day 14 reading. Brighteners providing complete protection (100% OAR) are cited with an asterisk.

[b]Brighteners were diluted in distilled water and used at 1% concentration. No mortality was observed among control insects (untreated or fed brightener).

To the surface of a 90 ml diet in a 180 ml container was added a 1 ml NPV inoculum at concentration of $5\times10^5$ polyhedral (PIB)/ml $C=1\times10^2$ PIB per $mm^2$ of diet surface. Additionally, to the inoculated diet was added 10 second-stage insect larvae (7 days old; x=25 mg). The insect larvae were incubated at 29° C. at about 50% relative humidity (RH) and a photoperiod LD 12:12 for 14 days in a clean air chamber. Mortality readings were then taken. In all tests both irradiated NPV (in $H_2O$) and non irradiated NPV (in $H_2O$) were used as virus controls. NPV in a 1% aqueous solution of brightener was adjusted to $5\times10^5$ PIB/ml and was irradiated for 60 minutes.

TABLE 2

Activity of gypsy moth NPV using selected fluorescent brighteners as UV screens.[a]

| | % larval mortality at days | | |
|---|---|---|---|
| Treatment used[b] | 7 | 10 | 14 |
| NPV + $H_2O$ (No UV) | 0.4 | 42.0 | 88.8 |
| NPV + $H_2O$ (60 UV) | 0.0 | 0.4 | 1.6 |
| NPV + $M_2R$ | 56.4 | 94.4 | 97.6 |
| CF | 4.8 | 73.6 | 92.4 |
| BS | 58.0 | 94.4 | 99.2 |
| BSB | 56.4 | 95.6 | 99.2 |
| BBY | 0.0 | 56.0 | 90.4 |
| CL | 0.0 | 35.2 | 89.6 |

TABLE 2-continued

Activity of gypsy moth NPV using selected fluorescent brighteners as UV screens.[a]

| | % larval mortality at days | | |
|---|---|---|---|
| Treatment used[b] | 7 | 10 | 14 |
| AR | 12.5 | 73.6 | 98.4 |

[a]NPV used at final concentration of $5 \times 10^5$ PIB/ml. Five replicates; 50 larvae per treatment per replicate.
[b]Brighteners were diluted in distilled water and used at 1% concentration. No mortality was observed among control larvae (untreated or fed brightener).

EXAMPLE 2

Inactivation Studies

UV radiation was provided to the test samples of EXAMPLE 1 using two 275 watt high intensity mercury lamps.

The 1 ml aliquots of NPV suspension were pipetted on to diet surface after exposure to UV for 60 minutes. After UV radiation, ten second-stage larvae (7 days old) were placed in each container for 14 days at 29° C., 50% RH, and a 12:12 photoperiod (L:D). The larvae were maintained in conditions as described above. Mortality readings were then taken. All tests were repeated five times, with 50 larvae per exposure period per replicate and 50 untreated controls per replicate. The percentage of original viral activity remaining (% OAR) was based upon mortality before ($LC_{90}$=100% OAR) and after UV radiation [Ignoffo and Batzer, J. Econ. Entomol., Vol. 64, (1971), pp. 850-853]. The length of UV radiation time that reduced NPV activity by about 75-80% (=about 20% OAR) was used for tests to evaluate the 23 fluorescent brighteners of the instant invention (Table 1). The brighteners were obtained as powders or liquids and were diluted in distilled water to 1% initial test in an NPV suspension standarized to contain an $LC_{90}$ (=about $5\times10^5$ PIB/ml on diet). NPV suspensions with or without fluorescent brighteners, were exposed to UV radiation for 60 minutes (min). Brighteners were compared with the unexposed NPV control ($LC_{90}$ at 0 min. UV radiation) as well as the exposed NPV control ($LC_{90}$ at 60 min. of UV radiation).

The relative efficiencies of brighteners as UV protectants were compared with the standard (water), and statistical differences were calculated by Duncan's multiple range test at the 5% probability level.

It can be seen that six of the brighteners, Calcofluor White $M_2R$ ($M_2R$), Intrawite CF (CF), Leucophor BS (BS), Leucophor BSB (BSB), Phorwite BBU (BBV), Phorwite CL (CL), and Phorwite AR (AR) provided complete UV radiation protection (100% OAR) at 1% concentration. In addition, NPV-caused mortality was significantly greater among larvae fed NPV+$M_2R$, NPV+BS, NPV+BSB, NPV+AR and NPV+CF [60 min. UV radiation (60 UV)] than nonirradiated NPV−$H_2O$ at days 7 and 10. Forty-two percent of total mortality occurred within 10 days among larvae fed on nonirradiated NPV, greater than 70% of total mortality occurred among larvae fed on NPV+AR and NPV+CF (60 UV), and more than 95% of the total mortality occurred among larvae fed NPV+BS, NPV+BSB, and NPV+$M_2R$ (60 UV).

The data show that several brighteners provide excellent protection at 1.00%. Four of these were evaluated at lower concentrations (see Table 3). All four stilbene fluorescent brighteners provided complete protection at about a 1% concentration. Calcofluor $M_2R$ and Phorwite AR were superior to Leucophor BS and Leucophor BSB and provided greater radiation protection at 0.100%, 0.010%, and 0.001%. At lower concentrations (0.100%), both $M_2R$ and AR provided excellent protection.

TABLE 3

Relationship between concentration of fluorescent brightener and radiation protection of LdMNPV.[a]

| Treatment used | Concentration used (%) | % of original activity remaining |
|---|---|---|
| NPV + $H_2O$ (No UV) | — | 100.0 |
| NPV + $H_2O$ (60 UV) | — | 1.1 |
| NPV + Br (60 UV) | | |
| +BSB | .001 | 1.1 |
| | .010 | 6.7 |
| | .100 | 74.2 |
| | 1.000 | 100.0 |
| +BS | .001 | 0.6 |
| | .010 | 7.9 |
| | .100 | 70.2 |
| | 1.000 | 100.0 |
| $M_2R$ | .001 | 14.0 |
| | .010 | 83.7 |
| | .100 | 100.0 |
| | 1.000 | 100.0 |
| +AR | .001 | 14.6 |
| | .010 | 71.9 |
| | .100 | 96.6 |
| | 1.000 | 100.0 |

The efficacy of NPV has been variable due to both intrinsic (i.e., low virulence, sensitivity to solar radiation) and extrinsic (i.e., application, formulation inadequacies) factors. Greater foliage protection and population control would occur if viral activity could be increased by selection of more virulent biotypes and is the subject of copending U.S. patent application Ser. No., 07/373,977 filed Jun. 30, 1989 [Shapiro, et al., J. Invertebr. Pathol., Vol. 16, (1970), pp. 107-111], by mutagens, [Reichelderfer and Benton., J. Invertebr. Pathol., Vol. 23, (1973), pp. 38-41], or by the addition of adjuvants [Doane and Wallis., J. Insect Pathol., Vol. 6, (1984), pp. 423-429].

Based upon the observation that virus-caused larval mortalities occurred sooner at days 7 and 10 among larvae exposed to NPV+brighteners (60 UV), bioassays were initiated to determine whether these viral activities were influenced by the addition of certain stilbene fluorescent brighteners.

EXAMPLE 3

BIOASSAY

Nuclear Polyhedrosis Virus: The bioassay procedure was followed essentially as described in Shapiro, Bell, Entomol. Soc. Am., Vol. 5, (1982), pp. 346-349 and incorporated herein by reference. In short, NPV was diluted in distilled water (virus control) or in an aqueous solution of fluorescent brightener. Virus suspensions were applied (1 ml) to the surface of the diet (180 ml/container) and 10 late-second instar larvae were placed in each container. Larvae were maintained for 21 days at 29° C., 50% RH, and a photoperiod of 12:12 (L:D). In the initial test, four brighteners ($M_2R$, AR, BS, and BSB) were evaluated as activity enhancers (see Table 4). The results were totally unexpected, since a virus concentration of 1000 PIB per ml per container+brightener (1%) caused 92 to 100% mortality, i.e., an increase in activity or more than 100-fold.

TABLE 4

Effects of selected fluorescent brighteners on gypsy moth NPV activity.

| Treatment used | NPV dose (PIB/ml) | No. of larvae | No. dead at day 21 |
|---|---|---|---|
| NPV + $H_2O$ | $10^3$ | 50 | 10 |
| | $10^4$ | 50 | 18 |
| | $10^5$ | 50 | 38 |
| | $10^6$ | 50 | 50 |
| | $10^7$ | 50 | 50 |
| NPV + $M_2R$ (1%) | $10^3$ | 50 | 50 |
| | $10^4$ | 50 | 50 |
| | $10^5$ | 50 | 50 |
| | $10^6$ | 50 | 50 |
| | $10^7$ | 50 | 50 |
| NPV + AR (1%) | $10^3$ | 50 | 50 |
| | $10^4$ | 50 | 50 |
| | $10^5$ | 50 | 50 |
| | $10^6$ | 50 | 50 |
| | $10^7$ | 50 | 50 |
| NPV + BS (1%) | $10^3$ | 50 | 45 |
| | $10^4$ | 50 | 50 |
| | $10^5$ | 50 | 50 |
| | $10^6$ | 50 | 50 |
| | $10^7$ | 50 | 50 |
| NPV + BSB (1%) | $10^3$ | 50 | 46 |
| | $10^4$ | 50 | 49 |
| | $10^5$ | 50 | 50 |
| | $10^6$ | 50 | 50 |
| | $10^7$ | 50 | 50 |

A second test was therefore set up with lower doses (i.e., $1\times10^1$, $1\times10^2$, so that the lethal concentration required to kill 50% of the test insects (=$LC_{50}$, see Table 5) as well as the time required for 50% of the test population to die from NPV (=$LT_{50}$, see Table 7) might be established.

TABLE 5

Effects of several fluorescent brighteners on gypsy moth NPV activity ($LC_{50}$)

| Treatment used[a] | $LC_{50}$ (PIB/ml) 7d | 14d | 21d |
|---|---|---|---|
| NPV + $H_2O$ | — | 105,052 | 17,801 |
| NPV + $M_2R$ (1%) | 156,306 | 54 | 10 |
| NPV + AR (1%) | 164,357 | 114 | 11 |
| NPV + BS (1%) | 130,841 | 55 | 13 |
| NPV + BSB (1%) | 131,752 | 274 | 27 |

[a]Each treatment consisted of five NPV dilutions; four replicates; 50 larvae per dilution per treatment per replicate. No mortality occurred in untreated control group or in control groups treated with fluorescent brighteners (1%).

TABLE 6

Effect of Calcofluor $M_2R$ upon gypsy moth NPV activity.

| Mortality levels (% Kill) | Treatment[a] NPV + $H_2O$ | NPV + Calcofluor $M_2R$ |
|---|---|---|
| 10 | 3,232 | 3 |
| 30 | 8,641 | 5 |
| 50 | 17,801 | 10 |
| 70 | 33,874 | 16 |
| 90 | 91,060 | 34 |

[a]Day 21 data; average concentrations required to cause 10, 30, 50, 70, 90% mortalities. (PIB/cup). Four replicates.

TABLE 7

Effects of several fluorescent brighteners upon gypsy moth NPV activity ($LT_{50}$)[a]

| Virus dose (PIB/ml) | $LT_{50}$ (days) following exposure to NPV + $H_2O$ | NPV + $M_2R$ | NPV + AR | NPV + BS | NPV + BSB |
|---|---|---|---|---|---|
| $1\times10^1$ | — | 21.0 | 19.7 | 20.7 | 24.9 |
| $1\times10^2$ | — | 12.7 | 15.7 | 13.1 | 15.3 |
| $1\times10^3$ | — | 10.6 | 10.7 | 10.1 | 12.7 |
| $1\times10^4$ | 24.7 | 9.4 | 9.3 | 8.7 | 10.1 |
| $1\times10^5$ | 14.2 | 7.0 | 7.5 | 6.9 | 6.8 |
| $1\times10^6$ | 11.2 | 5.0 | 4.7 | 5.5 | 4.8 |

[a]Fifty larvae per dilution per treatment per replicate; four replicates. No mortality occurred in untreated control groups or in control groups treated only with fluorescent brighteners (1%).

The average $LC_{50}$ of NPV+$H_2O$ at day 21 was greater than 17,000 PIB per cup, with values ranging from 14,700 to about 21,500 PIB per ml per cup. The average $LC_{50}$ of NPV+$M_2R$ was 10 PIB per cup, with values ranging from 9 to 13 PIB per cup. In other words, the $LC_{50}$ value was reduced by more than 1700-fold with the addition of Calcofluor $M_2R$. The addition of other brighteners enhanced activity from 659-fold (Leucophor BSB) to more than 1600-fold (Phorwite AR). When these materials alone were fed to gypsy moth larvae, none of the larvae died nor did any appear to be affected adversely, i.e., growth and development were normal. While boric acid [Shapiro and Bell, Ann. Entomol. Soc. Am., Vol. 75, (1982), pp. 346–349] and chitinase [Shapiro, et al., J. Econ. Entomol., Vol. 80, (1987), pp. 1113–1116] were shown to enhance the gypsy moth NPV activity, an increase of 1000-fold appears to be unprecedented.

When the data were analyzed in greater detail, the enhancement activity (specifically Calcofluor $M_2R$) is even more apparent (Table 6 and 7). While an increase in activity of almost 1800-fold was noted for the $LC_{50}$s, the difference became greater (i.e., about 2700-fold) for $LC_{90}$s. A 280-fold increase in NPV concentration was required to increase mortality from 10% (3232 PIB/cup) to 90% (91,060 PIB/cup) among larvae exposed to NPV+$H_2O$, while only about 11 times more NPV was needed to increase mortality from 10% (3 PIB/cup) to 90% (34 PIB/cup). In other words, the addition of Calcofluor $M_2R$ (1%) resulted in a much greater host susceptibility.

The time required for 50% of the test larvae to die from viral infection was reduced as NPV dose increased (Table 7). These results are not surprising and are typical with other NPVs that have been tested. Thus, the $LT_{50}$ decreased from 24.7 days ($10^4$ PIB/cup), to 11.2 days ($10^6$ PIB/cup) among larvae exposed to NPV+$M_2R$, NPV+AR, NPV+BS, and NPV+BSB, but the $LT_{50}$s were much lower in this test group. Direct comparisons can be made among larvae exposed to $10^4$, $10^5$, and $10^6$ PIB/cup only. In these instances, $LT_{50}$s were reduced from 24.7 days to an average of 9.4±0.5 days ($10^4$ PIB/cup), 14.2 days to an average of 7.1±0.3 days ($10^4$ PIB/cup), and from 11.2 to 5.0±0.3 days ($10^6$ PIB/cup) with the addition of the stilbene fluorescent brighteners to the gypsy moth PNV.

EXAMPLE 4

Cytoplasmic Polyhedrosis Virus: A cytoplasmic polyhedrosis virus (CPV), which is infectious for gypsy moth larvae was also tested (Table 8). While the virus is infectious ($LC_{50}$=137,000 PIB/ml), it is not nearly as virulent as the gypsy moth NPV (about 18,000 PIB/ml). The addition of Phorwite AR (1%), significantly reduced the $LC_{50}$ about 800-fold (i.e., $LC_{50}$=169 PIB/ml).

TABLE 8

| Effect of Phorwite AR upon gypsy moth CPV activity. | |
|---|---|
| Treatment used[a] | $LC_{50}$ (PIB/ml) |
| CPV + $H_2O$ | 136,923 |
| CPV + AR (1%) | 169 |

[a]Each treatment consisted of five CPV dilutions; four replicates; 50 larvae per dilution per treatment per replicate. No mortality occurred in the untreated control group or in the control group treated only with Phorwite AR (1%).

Since the CPV multiplies only in the cytoplasm of midgut epithelial cells, it is reasonable that the site of action of the brightener(s) is the midgut.

While the brightener(s) increase the activity of gypsy moth viruses (CPV, NPV) to gypsy moth larvae about 1000-fold, the question arose whether the gypsy moth larvae was unique in its response or whether other lepidopterous insects would react in a similar fashion.

EXAMPLE 5

Fall Armyworm

Nuclearpolyhedrosis Virus: The fall armyworm, an agriculturally important pest, is susceptible to an NPV (SfMNPV) and was also tested (Table 9). In this test three day old larvae were exposed to either NPV+$H_2O$ or NPV+Calcofluor $M_2R$ at NPV concentrations ranging from $1\times10^1$ to $1\times10^6$ PIB per ml (=$1\times10^0$ to $10^5$ PIB per cup) and tests were terminated at day 10.

TABLE 9

| Effect of Calcofluor $M_2R$ upon fall armyworm NPV activity. | |
|---|---|
| Treatment[a] | $LC_{50}$ (PIB/ml)[b] |
| NPV + $H_2O$ | 620,875 |
| NPV + $M_2R$ | 488 |

[a]Each treatment consisted of six NPV dilutions; two replicates; 20 larvae per dilution per treatment per replicate. No mortality occurred in untreated control group or in control treated only with Calcofluor $M_2R$
[b]$LC_{50}$ expressed in terms of PIB/ml; 0.1 ml of NPV suspension per cup.

The average $LC_{50}$ of SfMNPV+$H_2O$ at day 10 was greater than 620,000 PIB per ml (=62,000 PIB per cup), with values ranging from about 310,000 to about 1,250,000 PIB per ml (=31,000-125,000 PIB per cup). The average $LC_{50}$ of SfMNPV+$M_2R$ was about 490 PIB per ml (=about 50 PIB per cup), with values ranging from about 250 to about 1000 PIB per ml (=about 25-100 PIB per cup). In other words, the $LC_{50}$ value was reduced by almost 1300-fold with the addition of Calcofluor $M_2R$. These results with SfMNPV were very similar to those obtained with LdMNPV and indicate that these two unrelated lepidopterous insects (Family *Noctuidae for Spodoptera*, Family *Lymantriidae for Lymantria*) react in a similar fashion to the stilbene fluorescent brightener.

Granulosis Virus (GV): The fall armyworm GV was also tested: Stock suspension of fall armyworm granulosis virus was made by grinding up 50 large, granulosis-infected fall armyworm larvae in 50 ml of sterile distilled water. The first 100 fold dilution ($10^{-2}$) was made by adding 0.5 ml of GV suspension to 49.5 ml of sterile distilled water or 0.1% Calcoflour $M_2R$.

Subsequent 100 fold dilutions were made by adding 0.1 ml of dilution to 9.9 ml of sterile distilled water or 0.1% brightener to obtain dilutions of $10^{-4}$, $10^{-6}$, $10^{-8}$, and $10^{-10}$. The virus dilutions were applied to the surface of bean diet, without formalin, at the rate of 0.1 ml/cup (approximately 800 mm sq). Controls consisted of 0.1 ml per cup of sterile distilled water or 0.1% brightener. Two-day-old fall armyworm larvae were isolated in the treated cups, (30 cups per replication, 2 replications per dilution), and observed for 13 days. At this time healty larvae had pupated and GV-infected larvae had either died or showed obvious signs of infection such as paler color and puffy appearance and failure to pupate. Larvae that died from handling or other causes than the GV were substracted from the number treated.

The results in (Table 10) show that the chemical adjuvant enhanced the infectivity of the fall armyworm granulosis virus for fall armyworm larvae. The signs and symptoms of the granulosis virus were the same with the enhancer as without it. In both cases most mortality occurred in the final larval instar.

TABLE 10

| Effect of Calcofluor $M_2R$ upon SFGV activity[a] | | |
|---|---|---|
| Treatment | % mortality | |
| Virus dilution | SfGV + $H_2O$ | SfGV + Calcofluor |
| Control | 0.0 | 5.02 |
| $10^{-10}$ | 22.8 | 83.3 |
| $10^{-8}$ | 44.1 | 98.3 |
| $10^{-6}$ | 61.7 | 98.3 |
| $10^{-4}$ | 90.0 | 100.0 |
| $10^{-2}$ | 100.0 | 100.0 |

[a]2-day old larvae treated: 0.1 ml GV suspension per 800 $mm^2$ diet surface; 2 replicates; total = 60 larvae per dilution per treatment per replicate.

Iridescent Virus: Stock suspension of Heliothis virus was prepared by grinding up 8, half-grown iridescent virus infected, corn earworm (*Heliothis zea*) larvae in 8 ml of sterile distilled water. This stock suspension was designated as 1.0 and subsequent 10-fold dilutions as 0.1, 0.01, 0.001, 0.0001, 0.00001. The serial dilutions were made with sterile distilled water and with 0.1% Calcofluor $M_2R$. The viral dilutions were applied to the surface of bean diet, without formalin, at the rate of 0.1 ml per cup (approximately 800 mm sq).

Controls consisted of 0.1 ml per cup of sterile distilled water or they were untreated. Insects were observed until they either died or completed pupation. Because larval life may be prolonged or mortality may occur in the pupal stage and because virus-caused infection is not easily diagnosed by light microscopy, the criterion used for comparison was completion of development to the moth stage. Two replications of 30 cups each were set up. The number that died of injury form handling or causes other than iridescent virus were subtracted from the number treated.

The results shown in (Table 11) show that (based on the reduction in the number of moths when the virus was mixed in the brightener), the brightener increased infectivity of the iridescent virus.

TABLE 11

| Effect of Calcofluor $M_2R$ upon *Heliothis iridescent* virus activity.[a] | | |
|---|---|---|
| | % adult emergence | |
| Virus Dilution | IV + $H_2O$ | IV + Calcofluor |
| Control | 79.7% | 87.0% |
| .00001 IV | — | 82.1% |
| .0001 IV | 80.7% | 65.0% |
| .0010 | 86.4% | 57.1% |
| .0100 | 76.7% | 24.1% |
| .1000 | 63.2% | 15.8% |
| 1.00 | 43.8% | — |

[a]7 day old larvae treated; 0.1 ml IV suspension per 800 $mm^2$ diet surface; 2 replicates; total = 60 larvae per dilution per treatment per replicate.

EXAMPLE 6

Fall Armyworm Field Studies

(SfMNPV)

Test One

Whorl-stage field corn (Pioneer 3165) was infected with newly hatched fall armyworm larvae, *Spodoptera frugiperda*, at a rate of approximately 15 larvae per foot of row. A push type applicator was used to apply the larvae mixed in corn cob grits. Plots were arranged in a randomized complete block design with 5 replications. Plots were single rows 15 ft long with a row spacing of 36 in. (0.91 m). Treatments were separated by 3 rows of untreated corn and replications were separated by 10 ft of untreated corn. Treatments were applied to the corn three days after infestation in approximately 25 gal. water per acre (243 L/ha). The spray system consisted of a single 8003E TeeJet nozzle operating at 38 psi (262 kPa). The output was 0.29 gal/min (1.1 L/min) and the travel velocity was 167 ft/min (51 m/min). The spray was directed into the top of the corn plants from approximately 15 in. (38.1 cm) above the plants.

Treatments consisted of 4 concentrations of *Spodoptera frugiperda*) nuclear polyhedrosis virus (0, 5, 50, and 500 larval equivalents/ha (larval equivalent$=6\times10^9$ polyhedral inclusion bodies) in 3 concentrations of viral Calcofluor $M_2R$ (0, 0.1%, and 1.0%).

Two days after treatment, 10 corn plants were collected from each plot and brought to the laboratory. The plants were dissected and fall armyworm larvae were collected and held individually in 1 oz cups of bean diet. Thirty larvae were isolated from each plot and observed for mortality. Dead larvae were examined using phase contrast microscopy for presence of polyhedral inclusion bodies to determine if mortality was due to nuclear polynedrosis virus. Mortality due to causes other than NPV occurring within two days after collection was considered to be due to injury during collection and was subtracted from the number collected before the precent mortality due to treatment was calculated. Because there was a high incidence of natural parasitism, primarily by *Cotesia marginisen*, the number of larvae that produced parasitoids was also recorded.

Field tests showed that 1% fluorescent brightener increased mortality due to NPV at all levels of virus treatment (Table 12). However, 0.1% brightener significantly increased the virus mortality only at the lowest level of virus treatment (Table 12). There was no significant effect on parasitism due to the brightener although there was a significant effect on parasitism due to virus concentration (Table 13). This was because some larvae was killed by virus before the parasitoids could complete development.

TABLE 12

Percent mortality of fall armyworm larvae due to nuclear polyhedrosis virus after treatment with 4 concentrations of virus and 3 concentrations of fluorescent brightener.

| Virus concentration (LE/ha) | Fluorescent brightener concentration 0 | .1% | 1% |
|---|---|---|---|
| 0 | 0 | 0 | 0 |
| 5 | 5.5 | 17.2 | 15.5 |
| 50 | 26.0 | 26.6 | 36.9 |
| 500 | 58.9 | 48.6 | 72.3 |

TABLE 13

Percent mortality of fall armyworm larvae due to parasitoids after treatment with 4 concentrations of virus and 3 concentrations of fluorescent brightener.

| Virus concentration (LE/ha) | Fluorescent brightener concentration 0 | .1% | 1% |
|---|---|---|---|
| 0 | 36.4 | 35.1 | 27.9 |
| 5 | 36.1 | 33.1 | 38.7 |
| 50 | 21.2 | 27.3 | 23.2 |
| 500 | 14.9 | 23.2 | 6.7 |

Test Two

The second field test with the fluorescent brightener was designed to determine effect of increased coverage by using 50 gal. water per acre rather than 25 per acre and increasing the concentration of brightener. Again a radomized complete block design was used with single row plots 15 ft long. Newly hatched fall armyworm larvae were applied to the whorl-stage corn. Treatments were applied three days later, this time a 8006E TeeJet nozzle was used to increase amount of water applied. Treatments consisted of 1 concentration of nuclear polyhedrosis virus (50 larval equivalents per ha) in 4 concentrations of brightener (0, 0.1%, 1.0% and 5.0%) and a control plot which was treated with water alone.

Corn plants were collected and larvae isolated on bean diet two days after treatment. Thirty larvae were isolated per plot and mortality due to nuclear polyhedrosis virus was determined as before.

The second test showed again that 1% brightener increased the mortality due to NPV but increasing the brightener to 5% failed to increase mortality due to virus (Table 14). The 5% concentration of brightener may have deterred feeding by the larvae and thereby reduced the amount of virus ingested.

TABLE 14

Mortality of fall armyworm larvae due to nuclear polyhedrosis virus after treatment with 50 LE/ha of NPV in 4 concentrations of fluorescent brightener.

| Treatment: brightener concentration | Number larvae collected | Percent killed by NPV |
|---|---|---|
| 0 | 115 | 44.3 |
| .1% | 113 | 46.0 |
| 1.% | 106 | 63.2 |
| 5.% | 79 | 43.0 |

It can be seen there has been provided in accordance with the present invention, biocontrol compositions and methods for their use in the management of insect pests.

The invention as described by the specific embodiments is not to limit its scope. It is envisioned and apparent that many alternatives and variations may be encompassed by the present invention. It is intended that the spirit and scope of this disclosure include such alternatives and variations.

We claim:

1. A method of treating insect pests comprising applying an effective amount of a biocontrol composition to said pests, wherein said biocontrol composition comprises:

a) an amount of at least one virus entomopathogen effective for producing a lethal infection in an insect pest, and b) a chitin synthetase inhibitor capable of enhancing the lethal activity of said virus entomopathogens in an amount sufficient to provide such enhancement.

2. The method of claim 1, wherein the concentration of the chitin synthetase inhibitor is less than 5.0% w/v.

3. The method of claim 2, wherein the concentration of the chitin synthetase inhibitor is about 0.001 to about 1.000% w/v.

4. A method of treating insect pests comprising applying an effective amount of a biocontrol composition to said pests, wherein said biocontrol composition comprises:

a) an amount of at least one virus entomopathogen effective for producing a lethal infection in an insect pest, and b) a fluorescent brightener capable of enhancing the lethal activity of said virus entomopathogens in an amount sufficient to provide such enhancement.

5. The method of claim 4, wherein said fluorescent brightener is a compound selected from the group consisting of benzoxazoles, coumarins, naphthalenes, naphthalimides, pyrazolines and stilbenes.

6. The method of claim 5, wherein said fluorescent brightener is a stilbene compound or effective analog thereof.

7. The method of claim 6, wherein said stilbene compound is 4,4'-diamino-2,2'-stilbene disulfonic acid, salts or analogs thereof.

8. The method of claim 6, wherein the analogs are Calcofluor White $M_2R$, Intrawite CF, Leucophor BS, Leucophor BSB, Leucophor PAB, Palanil Brilliant White R, Phorwite AR, Phorwite BBU or Phorwite CL.

9. The method of any one of claim 4, wherein the concentration of the fluorescent brighteners is less than 5.0% w/v.

10. The method of claim 9, wherein the concentration of the fluorescent brightener is about 0.001 to about 1.000% w/v.

11. The method of claim 1, or 4 wherein the virus is selected from the group consisting of nuclear polyhedrosis viruses, cytoplasmic polyhedrosis viruses, entomopox viruses and granulosis viruses, and iridescent viruses.

12. The method of claim 11, wherein the virus is a nuclear polyhedrosis virus.

13. The method of claim 11, wherein the virus is a cytoplasmic polyhedrosis virus.

14. The method of claim 11, wherein the virus is an entomopox virus.

15. The method of claim 11, wherein the virus is a granulosis virus.

16. The biocontrol composition of claim 13, wherein the virus is an iridescent virus.

* * * * *